US005688822A

United States Patent [19]
Khanna et al.

[11] Patent Number: 5,688,822
[45] Date of Patent: Nov. 18, 1997

[54] HETEROARALKYL AND HETEROARYLTHIOALKYL THIOPHENOLIC COMPOUNDS AS INHIBITORS OF 5-LIPOXYGENASE

[75] Inventors: Ish Kumar Khanna, Vernon Hills; Michael Allan Stealey, Libertyville; Richard Mathias Weier, Lake Bluff, all of Ill.

[73] Assignee: G.D. Searle & Co., Chicago, Ill.

[21] Appl. No.: 597,778

[22] Filed: Feb. 7, 1996

Related U.S. Application Data

[63] Continuation of Ser. No. 328,212, Oct. 25, 1994.

[51] Int. Cl.$^6$ .................... A61K 31/40; A61K 31/415; A61K 31/42; C07D 263/58; C07D 235/22

[52] U.S. Cl. .................... 514/375; 514/367; 514/394; 514/395; 514/415; 548/221; 548/307.1; 548/310.1; 548/509

[58] Field of Search .................... 548/166, 169, 548/221, 310.1, 509, 307.1; 514/375, 367, 394, 395, 415

[56] References Cited

U.S. PATENT DOCUMENTS

| | | | |
|---|---|---|---|
| 4,692,532 | 9/1987 | Spivack et al. | 548/312 |
| 4,808,644 | 2/1989 | Spivack et al. | 524/94 |
| 5,081,253 | 1/1992 | Santilli et al. | 546/118 |
| 5,280,047 | 1/1994 | Mueller | 514/678 |

FOREIGN PATENT DOCUMENTS

| | | |
|---|---|---|
| 0 190 684 A2 | 8/1986 | European Pat. Off. |
| 0 417 745 A2 | 3/1991 | European Pat. Off. |
| 0 434 405 A1 | 6/1991 | European Pat. Off. |
| 0 479 631 A1 | 4/1992 | European Pat. Off. |
| 29 31 741 A1 | 2/1981 | Germany |
| 31 43 327 A1 | 6/1982 | Germany |
| 2-274681 | 1/1992 | Japan |

OTHER PUBLICATIONS

S. A. Zaotova, et al. "Synthesis and Biological Activity of Substituted Sulfides of Indole and Benzofuran", Khim.–Farm. Zh., 26 (1), 52–55.

Crawley GC, Dowell RL, Edwards PN, Foster SJ, McMillan RM, WalkerERH, Waterson D. J. Med. Chem. 35, 2600–2609 1992.

Gallin JI, Goldstein IM, Snyderman R. "Inflammation. Basic Principles and Clinical Correlates", Raven Press, New York, p. 1130 1992.

*Primary Examiner*—C. Warren Ivy
*Assistant Examiner*—Evelyn Huang
*Attorney, Agent, or Firm*—Fitzpatrick, Cella, Harper & Scinto

[57] ABSTRACT

Compounds of the formula:

$$\text{HO}\underset{R^1}{\overset{R^2}{\diagdown}}\!\!\!\!\!\!-\!\!\!\!\!\!\diagdown\!\!\!\!\!\!\!-\!\!\!\!\!\!\!\text{S}-(CH_2)_n-(CHOH)_p-(CH_2)_q-(S)_r-R^3$$

Formula I and the pharmaceutically acceptable salts thereof, pharmaceutical compositions comprising a therapeutically-effective amount of the compounds or salts in combination with a pharmaceutically-acceptable carrier and methods for treating 5-lipoxygenase mediated conditions, inflammation-associated disorders and allergies.

13 Claims, No Drawings

HETEROARALKYL AND HETEROARYLTHIOALKYL THIOPHENOLIC COMPOUNDS AS INHIBITORS OF 5-LIPOXYGENASE

This is a continuation application of co-pending application Ser. No. 08/328,212, filed on Oct. 25, 1994, pending.

BACKGROUND OF THE INVENTION

1. Field of the Invention

The present invention relates to heteroaralkyl and heteroarylthioalkyl thiophenolic compounds. More particularly, the present invention relates to the novel compounds of Formula I, which inhibit 5-lipoxygenase, to pharmaceutical compositions containing one or more of these compounds in combination with a pharmaceutically-acceptable carrier, and to medical methods of treatment employing these compounds.

2. Background Information

It is well recognized that arachidonic acid, an essential unsaturated fatty acid, is enzymatically oxygenated to various products, including, prostaglandins, thromboxanes, the 5-, 11-, 12- and 15-hydroxyeicosatetraenoic acids (HETEs, DIHETEs) and hydroperoxyeicosatetraenoic acids (HPETEs) and the leukotrienes, all of which have potent physiological effects. The leukotrienes, which are produced via the 5-lipoxygenase pathway, are major contributors to the onset of the symptoms of asthma, and mediators for immediate hypersensitivity reactions, inflammation and other allergic responses.

Leukotrienes are found in inflammatory exudates, and are involved in the process of cellular invasion during inflammation. The term "leukotrienes" is used as a generic term to describe a class of substances, such as slow-reacting substance (SRS) which is an important mediator in asthma and other hypersensitivity reactions. Immunologically generated SRS is usually referred to as slow-reacting substance of anaphylaxis (SRS-A). SRS-A consists of leukotrienes (LT) known as $A_4$, $B_4$, $C_4$, $D_4$, and $E_4$. $LTC_4$ is at least 100 times more potent than histamine in causing long lasting bronchoconstricting effects. The leukotrienes also increase vascular permeability and cause decreased cardiac output and impaired ventricular contraction. $LTB_4$ may be an important mediator of inflammation in, for example, inflammatory bowel disease.

Chemotaxis is a reaction by which the direction of migration of cells is determined by substances in their environment. It is one of the major processes bringing leukocytes from the blood to an inflammatory site, whether the inflammation is caused by an infectious agent, allergic challenge, or other pro-inflammatory stimuli. $LTB_4$ is not only chemotactic for neutrophils and monocytes, but is also highly active in stimulating eosinophil locomotion. $LTB_4$ also stimulates calcium influx and aggregation of polymorphonuclear leukocytes and $LTB_4$ may, thus, play an important role in mediating both acute and chronic inflammation.

Rheumatoid spondylitis is characterized by an acute neutrophil flareup in the joint which is associated with elevated levels of $LTB_4$. $LTB_4$ is also present in gouty effusions, and exposure to urate crystals is known to stimulate $LTB_4$ production by neutrophils. Accordingly, the 5-lipoxygenase inhibitors of the present invention through inhibition of neutrophil attraction and activation in arthritic joints should reduce the protease and oxidative burden believed responsible for joint destruction in arthritic diseases.

Aspirin and the other non-steroidal anti-inflammatory agents (NSAIDs) such as indomethacin, ibuprofen, fenoprofen, and the like, inhibit the synthesis of prostaglandins via the cyclooxygenase pathway of arachidonic acid metabolism. These prostaglandin synthetase inhibitors generally exhibit anti-inflammatory, anti-pyretic and analgesic activity, and are widely used in the treatment of arthritis. The non-steroidal anti-inflammatory agents can lead to the formation of additional pro-inflammatory derivatives of arachidonic acid produced through the 5-lipoxygenase pathway which play a role in immediate hypersensitivity reactions and also have pronounced inflammatory effects. Administration of the NSAIDs alone can produce allergic reactions including bronchospastic reactivity, skin rashes, syndrome of abdominal pain, fever, chills, nausea and vomiting, and anaphylaxis. For this reason, aspirin and the other non-steroidal anti-inflammatory agents (NSAIDs) are generally contraindicated for patients suffering from asthma, or who have previously exhibited allergic sensitivity to aspirin or other NSAIDs. Co-administration of the 5-lipoxygenase inhibitors of this invention with cyclooxygenase inhibitors may mitigate the untoward side effects of the latter and allow the increased advantageous use of such cyclooxygenase inhibitors.

Prior to the recognition of the significance of the 5-lipoxygenase pathway of arachidonic acid metabolism in allergic reactions and inflammation, the search for effective therapeutic agents was based primarily on those agents which treated the symptoms of allergy and inflammation. There has since been effort to develop new drugs which selectively block the formation of the mediators of these conditions, and the present invention provides new chemical entities which are inhibitors of the 5-lipoxygenase pathway, and are useful in the treatment of asthma, rheumatoid arthritis, psoriasis, and other allergic, hypersensitivity, and inflammatory conditions.

See Bengt Samuelsson, "Leukotrienes: Mediators of Immediate Hypersensitivity Reactions and Inflammation", *Science*, Vol. 220, pp. 568–575 (May 1983); Michael K. Bach, "Inhibitors of Leukotriene Synthesis and Action", *The Leukotrienes, Chemistry and Biology*, pp 163–194 (Academic Press, Inc., 1984); C. W. Lee et al., "Human Biology and Immunoreactivity of Leukotrienes", *Advances in Inflammation Research*, Volume 6, pp 219–225 (Raven Press, New York 1984); Editorial, "Leukotrienes and other Lipoxygenase Products in the Pathogenesis and Therapy of Psoriasis and Dermatoses", *Arch. Dermatol*, Vol. 119, pp 541–547 (July, 1983); Robert A. Lewis et al., "A Review of Recent Contributions on Biologically active Products of Arachidonate Conversion", *Int. J. Immunopharmac.*, Vol. 4, No. 2, pp 85–90 (1982); Michael K. Bach, *Biochemical Pharmacology*, Vol. 33, No. 4, pp 515–521 (1984); E. L. Becker, *Chemotactic Factors of Inflammation*, pp 223–225 (Elsevier Science Publishers B. V., Amsterdam, 1983); P. Sharon and W. F. Stenson, *Gastroenterology*, Vol. 86, 453–460 (1984); and Musch, M. W. et al., *Science*, Vol. 217, 1255 (1982), each of which is incorporated herein by reference.

U.S. Pat. No. 4,692,532 discloses substituted N-(4-Hydroxyphenylthioalkyl)cyclic imides.

U.S. Pat. No. 4,808,644 discloses substituted (4-Hydroxyphenylthioalkyl) derivatives.

European Patent Application Publication Number 0 434 405 A1 discloses imidazo[4,5-c]pyridines.

Japanese Patent Application No. 04001177 discloses the preparation of sulfonium compounds as hardening initiators.

Zotova et al., "Synthesis and Biological Activity of Substituted Sulfides of Indole and Benzofuran," *Khim.-Farm.*

Zh., 26(1), 52–5, disclose the synthesis of substituted sulfides of indole and benzofuran.

Each of the documents described hereinabove discloses compounds which are structurally different from the compounds of the present invention. Thus, the compounds of the present invention are structurally distinct from that which has been described in the art.

SUMMARY OF THE INVENTION

The present invention provides compounds having a structure of Formula I:

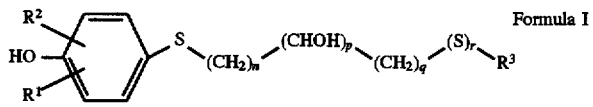

and the pharmaceutically acceptable salts thereof, wherein:

$R^1$ and $R^2$ are each alkyl;

n is an integer of from 1 to 5;

p is an integer of from 0 to 1;

q is an integer of from 0 to 3;

r is an integer of from 0 to 1; and $R^3$ is a bicyclic group, with the proviso that when $R^1$ and $R^2$ are each alkyl, and p, q and r are each O, $R^3$ is not a napthylmethyl group.

DETAILED DESCRIPTION OF THE PREFERRED EMBODIMENTS

(1) Description of Invention

In one aspect, the present invention provides compounds comprising a structure of Formula I, as described above, and pharmaceutically-acceptable salts thereof.

Specific compounds within the scope of the invention include, but are not limited to, the compounds discussed in the examples presented below, as well as their pharmaceutically-acceptable salts.

Contemplated equivalents of the compounds described in Formula I include compounds which otherwise correspond thereto, and which have the same general properties thereof, wherein one or more simple variations of substituents are made which do not adversely affect the efficacy of the compound.

Certain compounds of the present invention may contain a basic functional group, such as amino and the like, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarat, succinate, tartrate, napthylate, mesylate, glucoheptonate, lactobionate, and laurylsulphonate salts and the like. (See, for example, S. M. Berge et al., "Pharmaceutical Salts," J. Pharm. Sci., 66, 1–19 (1977), which, as well as all other documents referred to herein, is incorporated herein by reference.)

In other cases, the compounds of the invention may contain one or more acidic functional groups, such as carboxyl and the like, and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can be prepared in situ during the final isolation and purification of the compounds, or by separately reacting the purified compound in its free acid form with a suitable base, such as the hydroxide, carbonate or bicarbonate of a metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, S. M. Berge et al., "Pharmaceutical Salts," J. Pharm. Sci., 66, 1–19 (1977), which is incorporated herein by reference).

In another aspect, the present invention provides pharmaceutically-acceptable compositions which comprise a therapeutically-effective amount of one or more of the compounds of Formula I, as described herein, formulated together with one or more pharmaceutically-acceptable carriers. The pharmaceutical compositions of the invention may be specially formulated for oral administration in solid or liquid form, or in the form of an aerosol for inhalation, for parenteral injection, or for rectal or vaginal administration.

The present invention also comprises methods for treating 5-lipoxygenase mediated conditions, such as inflammation, or inflammation-associated disorders, and allergies in an animal, the method comprising administering to the animal having such condition a therapeutically-effective amount of a compound of Formula I.

The most preferred embodiment of the invention is the compound described in Example 14 below.

Certain compounds of this invention may exist in geometric or stereoisomeric forms. The present invention contemplates all such compounds, including cis- and trans-geometric isomers, R- and S-enantiomers, diastereomers, d-isomers, l-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

(2) Definitions

For purposes of clarity, the terms and phrases used throughout this specification and the appended claims are defined in the manner set forth directly below.

Some of the chemical structures which are presented in this specification and the appended claims have been drawn using the convention which employs lines to represent alkyl radicals, which is known by those of skill in the art.

The abbreviation "AIBN" as used herein means azobisisobutyronitrile.

The term "alkyl" as used herein defines straight or branched chain monovalent hydrocarbon radicals having between about 1 to about 10 carbon atoms, within which includes from about 1 to about 6 carbon atoms, and further within which includes from about 1 to about 3 carbon atoms. Representative alkyl radicals include, for example, methyl, ethyl, propyl, isopropyl, butyl, t-butyl, sec-butyl, isobutyl, pentyl, 1-methylbutyl, isopentyl, neopentyl, hexyl, octyl, nonyl, decyl, t-pentyl, etc.

The term "animal" as used herein includes mammals and nonmammals, and further includes humans and nonhuman mammals.

The term "bicyclic group" as used herein means a double ring structure comprising two 6-membered rings, two 5-membered rings or one 6-membered ring and one 5-membered ring (in any order), each of the two rings independently containing one, two or three double bonds, and the double ring structure containing 1, 2 or 3 nitrogen atoms and, optionally, containing further substitutions of up to 2 groups selected from oxygen, —NH, —N-alkyl and

Representative bicyclic groups include 1(H)-imidazo[4,5-c] pyridine, 1(H)-imidazo-[4,5-b]pyridine, benzimidazole, benzoxazole and the like.

The abbreviation "b.p." as used herein means boiling point.

The term "composition" as used herein means a product which results from the combining of more than one element or ingredient.

The abbreviation "DMA" as used herein means dimethylacetamide.

The abbreviation "DMF" as used herein means dimethylformamide.

The abbreviation "DMSO" as used herein means dimethylsulfoxide.

The abbreviation "DSC" as used herein means Differential Scanning Calorimetry.

The abbreviation "DTT" as used herein means dithiothreitol.

The abbreviation "EDTA" as used herein means ethylene diamine tetraacetic acid.

The abbreviation "EtOH" as used herein means ethanol.

The term "halogen" as used herein means chlorine, bromine, fluorine, and iodine.

The abbreviation "HETE" as used herein means hydroxyeicosatetraenoic acid.

The abbreviation "HPETE" as used herein means hydroperoxyeicosatetraenoic acid.

The term "heteroatom" as used herein means an atom of any element other than carbon or hydrogen.

The abbreviation "HPLC" as used herein means High Pressure Liquid Chromatography.

The abbreviation "ip" as used herein means intraperitoneal.

The abbreviation "MeOH" as used herein means methanol.

The abbreviation "mp" as used herein means melting point.

The abbreviation "mpk" as used herein means milligrams per kilogram.

The abbreviation "MPO" as used herein means myeloperoxidase.

The abbreviation "NMR" as used herein means Nuclear Magnetic Resonance.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, as defined directly above, such as a liquid or solid filler, diluent, excipient, solvent or encapsulating material, involved in carrying or transporting a chemical compound or pharmaceutical agent from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laureate; (13) agar; (14) buffering agents, such as magnesium hydroxide and aluminum hydroxide; (15) alginic acid; (16) pyrogert-free water; (17) isotonic saline; (18) Ringer's solution; (19) ethyl alcohol; (20) phosphate buffer solutions; and (21) other non-toxic compatible substances employed in pharmaceutical formulations.

The expression "pharmaceutically acceptable salts" is intended to include those salts capable of being formed with the compounds of the present invention without materially altering the covalent chemical structure thereof. Such salts include inorganic and organic base or acid addition salts, such as sodium, potassium, calcium, ammonium, alkylammonium, quaternary ammonium, triethanolamine, lysine, hydrochloride, hydrobromide, phosphate, citrate, etc. well known to those skilled in the art. The foregoing salts are prepared in the conventional manner by neutralization of the compounds of formula I with the desired base or acid.

The abbreviation "t-Bu" as used herein means tert-butyl.

The phrase "therapeutically-effective amount" as used herein means an amount of a compound, material, or composition which is an effective dose for eliminating or ameliorating pain in an animal, or for producing some other desired therapeutic effect, at a reasonable benefit/risk ratio applicable to any medical treatment.

The phrases "title compound," "title product" and "title material" as used herein mean that compound, product or material whose chemical name is given, example, or subpart thereof, referred to. If no particular example, or subpart thereof, is referred to, it means that compound, product or material whose chemical name is given, and/or whose structure is shown, in the particular example, or subpart thereof, in which it appears.

The abbreviation "TPA" as used herein means tetradecanoylphorbol 13-acetate.

(3) Utility

The present invention provides compounds which block the 5-lipoxygenase metabolic pathway and, therefore, block the formation of the leukotrienes responsible for allergy and inflammation, and represent therapeutic agents which are useful in the treatment of allergic and hypersensitivity reactions and inflammation, alone, or also may be utilized in combination with other lipoxygenase inhibitors or with cyclooxygenase inhibitors, such as the non-steroidal anti-inflammatory agents.

The compounds of Formula I which inhibit 5-lipoxygenase are useful in treating 5-lipoxygenase mediated conditions, such as inflammation and inflammation-associated disorders and allergies and related disorders and conditions, such as arthritis, asthma, and psoriasis.

Compounds of the present invention would be useful for the treatment of inflammation in an animal, and for treatment of other inflammation-associated disorders, such as an analgesic in the treatment of pain and headaches, or as an antipyretic for the treatment of fever. For example, compounds of the present invention would be useful to treat arthritis, including but not limited to rheumatoid arthritis, spondyloarthopathies, gouty arthritis, systemic lupus erythematosus, osteoarthritis and juvenile arthritis. Such compounds would be useful in the treatment of asthma, bronchitis, menstrual cramps, tendinitis, bursitis, and skin related conditions such as psoriasis, eczema, burns and dermatitis. Compounds of the present invention also would be useful to treat gastrointestinal conditions such as inflammatory bowel syndrome, Crohn's disease, gastritis, irritable bowel syndrome and ulcerative colitis. Compounds of the present invention would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, hypersensitivity, conjunctivitis, gingivitis, swelling occurring after injury, myocardial ischemia, and the like. Compounds of the present invention are useful as anti-inflammatory agents, such as for the treatment of arthritis, with the additional benefit of having significantly less harmful side effects.

(4) Dosage and Mode of Administration

The compounds of the present invention can be administered to a patient in such oral dosage forms as tablets, capsules, pills, powders, granules, elixirs, or syrups as well as aerosols for inhalation. Likewise, administration may be effected intravascularly, subcutaneously, topically, or intramuscularly using dosage forms known to those of ordinary skill in the pharmaceutical arts. In general, the preferred form of administration is oral. An effective but non-toxic amount of the compound is employed in treatment. The dosage regimen utilizing the present compounds is selected in accordance with a variety of factors including the type, age, weight, sex, and medical condition of the patient, the severity of the condition to be ameliorated, and the route of administration. A physician of ordinary skill can readily determine and prescribe the effective amount of the drug required to prevent, treat or arrest the progress of the condition.

Dosages of the compounds of the present invention, will range generally between 0.1 mg/kg/day to about 100 mg/kg/day, and preferably between about 0.5 mg/kg of body weight per day to about 50 mg/kg of body weight per day, when administered to patients suffering from inflammation or allergic or hypersensitivity reactions. In general, a unit dose form of the compounds of the invention will contain from about 1.75 to about 750 mg of compound. The compound may be administered in divided dosages, e.g. two or more times daily. The compounds may also be administered transdermally or topically to treat proliferative skin conditions such as psoriasis. The daily dosage may be administered in a single dose or in equal divided doses three or four times daily.

Unit dosage forms such as tablets and capsules can contain any suitable, predetermined, therapeutically effective amount of one or more active agent and a pharmaceutically acceptable carrier or diluent. Generally speaking, solid oral unit dosage forms and other unit dosage forms of the compounds of this invention will contain from 1.75 to 750 mg per tablet of drug as the effective lipoxygenase inhibiting amount of the compound.

In the case of acute allergic or hypersensitivity reactions, it is generally preferable to administer the initial dosage via the parenteral route and continue parenteral administration until the patient is stabilized, and can be maintained, if necessary, on oral dosing.

In the case of psoriasis and other skin conditions, it may be preferred to apply a topical preparation of a compound of this invention to the affected area three or four times daily.

In treating asthma and arthritis with a compound of this invention, the compounds may be administered either on a chronic basis, or as symptoms appear. However, in the case of arthritis and other inflammatory conditions which can lead to deterioration of joints and malformations, it is generally preferable to administer the active agent on a chronic basis.

A typical tablet of this invention can have the following compositions:

| Ingredient | Mg/tablet |
| --- | --- |
| Active ingredient | 100 |
| Starch, U.S.P. | 57 |
| Lactose, U.S.P. | 73 |
| Talc, U.S.P. | 9 |
| Stearic acid | 12 |

In the pharmaceutical compositions and methods of the present invention, at least one of the active compounds of the invention, or a pharmaceutically acceptable salt thereof, will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug component may be combined with any oral non-toxic pharmaceutically acceptable inert carrier such as lactose, starch, sucrose, cellulose, magnesium stearate, dicalcium phosphate, calcium sulfate, mannitol and the like. For oral administration in liquid form, the active drug component may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like.

(5) Methods of Preparation

In general, the compounds of the present invention may be prepared by the methods illustrated in the following general reaction schemes, or by modifications thereof, from readily available starting materials in a conventional manner. Unless otherwise specified, the various substituents of the compounds are defined in the same manner as they are defined hereinabove in Formula I.

If a particular enantiomer of a compound of the present invention is desired, it may be prepared by chiral synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The compounds of the present invention may be synthesized by the procedures described in General Reaction Schemes 1, 2 and 3 presented hereinbelow.

General Reaction Schemes 1, 2 and 3 describe the general methods for synthesizing the compounds of the present invention wherein $R^1$ and $R^2$ are each alkyl, n is an integer of from 1 to 5, p is an integer of from 0 to 1, q is an integer of from 0 to 3, r is an integer of from 0 to 1 and $R^3$ is a bicyclic group.

The compounds of Formula I (wherein p and q=0) can be synthesized in the manner shown in General Reaction Scheme 1. Substituted 4-hydroxythiophenols (II) are alkylated with, for example, 3-bromo-1-propanol, 2-bromoethanol or ethylene oxide to give the hydroxy compounds III. This alkylation reaction is carried out in the presence of a non-nucleophilic base, such as sodium carbonate, potassium carbonate, sodium bicarbonate or diisopropylethylamine, using a solvent such as acetone, dimethylformamide or dimethylacetamide. Compounds III can also be synthesized by reacting compounds II with haloalkyl esters, such as methyl 4-bromobutyrate or 4-bromobutyric acid, to give compounds IV, followed by reduction with reducing agents, such as lithium borohydride for an ester or borane-tetrahydrofuran for a carboxylic acid. The alcohols III are converted to bromide derivatives V using a triarylphosphine, such as triphenylphosphine, in combination with a bromine source, such as carbon tetrabromide. This reaction is preferably carried out in an ethereal solvent, such as diethyl ether, tetrahydrofuran or dioxane at 20°–50° C. Alternatively, the alcohols III may be first converted to sulfonate esters by reaction with a suitable sulfonylating agent, such as p-toluenesulfonyl chloride, benzenesulfonyl chloride or trifluoromethanesulfonic anhydride, followed by treatment with a bromide salt, such as lithium bromide, sodium bromide or potassium bromide. The bromo compounds V are then reacted with the heterocycle to give the target compounds VI. When compounds VI are reacted with 1(H)-imidazo[4,5-c]pyridine in the absence of an additional base, the product of alkylation at the pyridine nitrogen predominates.

Alternatively, as illustrated in General Reaction Scheme 2, a heterocyclic compound, such as indole, benzimidazole, 1(H)-imidazo[4,5-c]pyridine or 2-mercaptobenzoxazole, may be first alkylated with, for example, 1-iodo-3-chloropropane, to give compounds VII. This reaction is preferably carried out in a solvent such as dimethylformamide or dimethylacetamide using a base such as sodium hydride or potassium hydride. The intermediates VII are then alkylated with the substituted 4-hydroxythiophenols II using procedures as described for the first step of General Reaction Scheme 1 to give the desired compounds VI.

The compounds of Formula I can also be synthesized by following General Reaction Scheme 3. The substituted 4-hydroxythiophenols II are alkylated with an unsaturated alkyl halide or sulfonate ester, such as $X(CH_2)nCH=CH_2$ (X=Br, Cl, I, or $OSO_2R$; n=1–5; R=phenyl, p-methyl phenyl, methyl or —$CF_3$) to give compounds VIII using conditions described for the first step of General Reaction Scheme 1. The epoxidation of compounds VIII using an oxidizing agent, such as m-chloroperoxybenzoic acid, followed by reaction with the appropriately substituted heterocycle gives the target compounds I. Alternatively, the appropriately substituted heterocycles may be reacted with the halohydrins X to give the target compounds I. The intermediates X can be synthesized by opening of epoxides IX with, for example, bromotrimethylsilane, hydrogen chloride or hydrogen bromide. In compounds of the present invention where n=1, the halohydrins X can be directly synthesized by reaction of compounds II with epichlorohydrin.

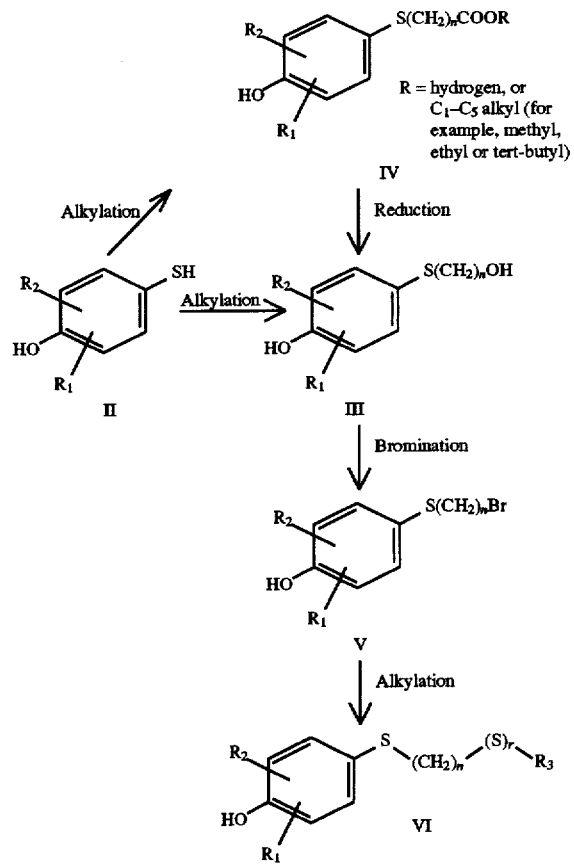

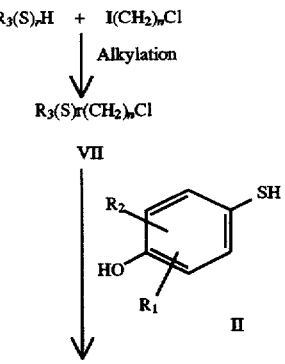

-continued
GENERAL REACTION SCHEME 2

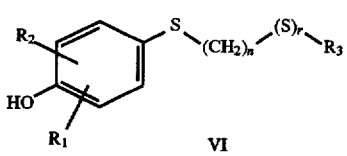

GENERAL REACTION SCHEME 3

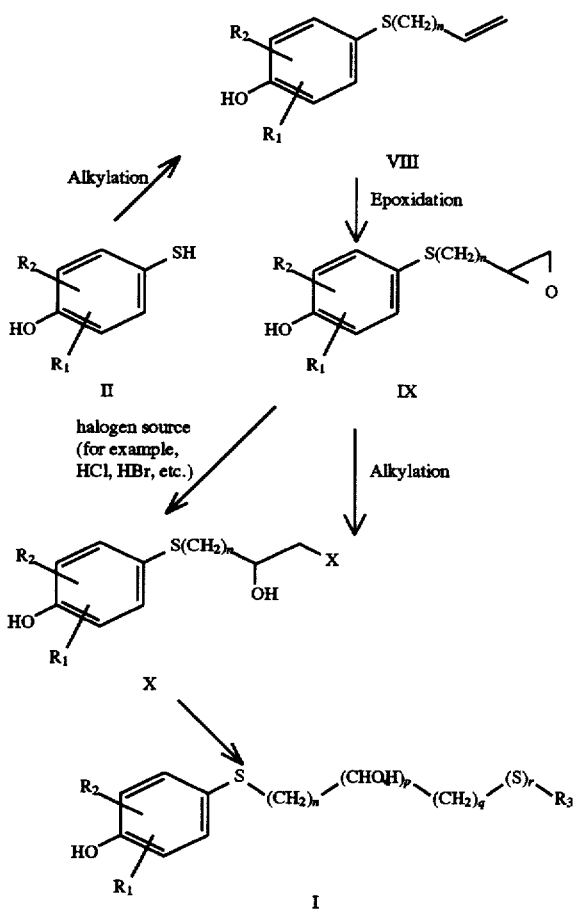

The conditions for carrying out the individual steps in each of the general reaction schemes presented above are conventional, well-known, and capable of wide variation.

Other methods known in the art can also be used to synthesize the compounds of the present invention.

(6) Biological Evaluations (a) Recombinant 5-Lipoxygenase Inhibition Assay

The compounds of the present invention were evaluated with respect to 5-lipoxygenase inhibition according to the Recombinant 5-Lipoxygenase Inhibition Assay described below.

Preparation of Human Recombinant 5-Lipoxygenase

Human 5-lipoxygenase expressed in E. coli as a soluble protein was prepared in the manner described by M. Noguchi et al., "Expression of Human 5-Lipoxygenase cDNA in E. Coli," FEBS Letters, Vol. 249, No. 2, 267–270 (1989), which is incorporated herein by reference. The human 5-lipoxygenase was partially purified by ion exchange chromatography and stored in 50 mM Tris-HCl buffer (pH 8.1) containing 150 mM NaCl, 2 mM EDTA, 2 mM DTT, and 50% glycerol at −70° C. before use.

Materials

The following solutions were prepared as indicated: $CaCl_2$/ATP, 12.5 mM $CaCl_2$ and 5 mM ATP in $H_2O$; arachidonic acid, 4 mM in ethanol; potassium phosphate buffer, 50 mM potassium phosphate and 0.1 mM EDTA, pH 7.2. Test compounds were first prepared at 10 mM in DMSO and further diluted to desirable concentrations with DMSO.

Assay of 5-Lipoxygenase Activity

The assay was carried out in a quartz cuvette to which 15 μl $CaCl_2$/ATP, 7.5 μl arachidonic acid, 7.5 μl ethanol or test compound, and 710 μl potassium phosphate buffer, in that order, were added and mixed. The mixture was prewarmed to 25° C. The enzymatic reaction was started by adding 10 μl of 5-lipoxygenase enzyme (~0.2 mg protein), and the formation of the reaction product 5-HPETE/5-HETE at 25° C. for 8 minutes was determined by measuring the increase in the absorbance at 240 nm using a Beckman DU-7 spectrophotometer.

The results for this assay are presented in Table 1 hereinbelow. The results for this assay are expressed in terms of activity with respect to 5-lipoxygenase inhibition as an $IC_{50}$ value (50% inhibitory concentration).

(b) Tetradecanoylphorbol Acetate (TPA) Assay

The compounds of the present invention were evaluated with respect to 5-lipoxygenase inhibition according to the Tetradecanoylphorbol Acetate (TPA) Assay which is described in Rao et al., "Comparative Evaluation of Arachidonic Acid (AA)-And Tetradecanoylphorbol Acetate (TPA) -Induced Dermal Inflammation." Inflammation, Vol. 17, No. 6, 723–741 (1993), which is incorporated herein by reference.

AA (arachidonic acid) and TPA (12-0-tetradecanoylphorbol 13-acetate, a protein kinase C activator) are widely employed agents to induce cutaneous inflammation in experimental animals.

The initiation of inflammatory responses by metabolites of AA via CO (cyclooxygenase) and LO (lipoxygenase) pathways, and suppression of acute inflammatory responses by inhibitors of CO and LO have established a role for metabolites of AA in acute inflammation.

In this study, selective 5-lipoxygenase inhibitors, such as zileuton, MK-886, $LTB_4$ and $LTD_4$ receptor agonists were evaluated in acute inflammatory responses elicited by the topical application of TPA to the ears of mice. The increases in edema and myeloperoxidase (MPO) were used as readouts of inflammatory responses.

Animals.

Female BALB/c mice (17–25 g; Jackson Labs, Bar Barbor, Ma.) or male Swiss Webster mice (Charles River, Portage, Mich.) were used in the studies. The animals were housed in a vivarium with a 12-hour lighting schedule (0600–1800 hours on) with free access to food and water. Housing and experimental procedures were conducted according to institutionally approved (Monsanto, St. Louis, Mo. and National Institute of Health) guidelines.

Drugs and Reagents

Hexadecyltrimethylammonium bromide (HTAB), and TPA were purchased from Sigma Chemical Co. (St. Louis, Mo.). Human polymorphonuclear leukocyte myeloperoxidase (20 units/mg protein) was obtained from Calbiochem (San Diego, Calif.). One unit of MPO was defined as the activity of the enzyme that oxidizes 1 μmol of hydrogen peroxide per minute at 25° C.

TPA Inflammation Model.

Groups of mice (six to eight per treatment) received either vehicle (saline or 0.5% w/v methylcellulose or saline with 1% alcohol as appropriate) or drug intraperitoneally 60 minutes after the topical application of TPA [4 μg/ear applied as a solution in acetone (200 μg/ml), 10 μl each to the inner and outer surface of ear]. The control group received 20 μl of acetone as a topical application. Four hours following the application of TPA, increases in ear thickness were measured and ears were excised for MPO measurements.

Measurement of MPO.

Ear samples were homogenized in a Brinkman polytron in 3 ml of 50 mM potassium phosphate buffer (pH 6.0), centrifuged (32,000 g, 20 minutes), and supernatants were discarded. Tissue pellets were reextracted into potassium phosphate buffer (50 mM, pH 6.0) with 0.5% HTAB, frozen-thawed three times, and centrifuged to collect supernatants that were used in MPO assays. MPO assays were performed according to the procedures described by Bradley et al. [Bradley, P. B., et al. "Measurement of cutaneous inflammation: Estimation of neutrophil content with an enzyme marker," *J. Invest. Dermatol.* 78:206–209 (1982)], adapted to a 96-well plate format. Briefly, 7 μl of unknowns or human neutrophil MPO standards were added to a 96-well plate. The reaction was initiated by the addition of 200 μl of assay buffer containing 0.167 mg/ml o-dianisidine and 0.0005% hydrogen peroxide. The rate of change of absorbance was monitored in kinetic mode by a plate reader (Molecular Devices, Menlo Park, Cailf.). Levels of MPO in lavage samples were determined from the calibration curves using human neutrophil MPO as the reference standard. The levels of MPO were expressed as milliunits per ear. Measurements of MPO, a granular constituent of neutrophils, were taken as indices of neutrophil influx into the inflamed tissue. MPO constitutes nearly 5% of neutrophil content and the utility of its measurements to correlate neutrophil influx is well established.

Data Analyses.

Ear thickness measurements were averaged and responses in vehicle-treated groups were subtracted from those in other treatment groups to give inflammatory responses. The percent inhibition was defined by the following equation:

$$\% \text{ inhibition} = \frac{(C_r - T_r)}{(C_r)} \times 100$$

where $C_r$ and $T_r$ refer to increases in ear thickness in arachidonic acid- (or TPA-) treated and arachidonic acid- (or TPA-)+drug-treated groups, respectively. The data were analyzed by a one-way analysis of variance followed by a Neuman-Keuls or a parametric Dunnett's test, as known by those of skill in the art.

The results for this assay are presented in Table 1 hereinbelow. The results for this assay are expressed in terms of activity with respect to 5-lipoxygenase inhibition as a per cent inhibition value. A test compound which is active in this assay inhibits or prevents the increase in ear thickness induced by treatment with TPA.

(c) $LTB_4$ and Thromboxane Production by Calcium Ionophore Stimulated Human Blood—Human Whole Blood $LTB_4$ Assay The compounds of the present invention were evaluated with respect to 5-lipoxygenase inhibition according to the Human Whole Blood $LTB_4$ Assay described below.

Human whole blood was collected in heparin containing Vacutainer brand tubes. The blood was diluted with RPMI-1640 cell culture media [1:4] (Gibco, Grand Island, N.Y.) and 200 microliters were added per well in 96 well microtiter plates. Compounds of the present invention diluted in dimethylsulfoxide were added to the blood and allowed to incubate for 15 minutes at 37° C. in a humidified incubator. Calcium ionophore A23187 [20 mcg/ml final concentration, Sigma Chemical Co., St. Louis, Mo.] was added, and the incubation was continued for 10 minutes. The incubation was terminated by centrifugation [833 g, 10 minutes at 4° C]. Supernatants were analyzed for $LTB_4$ and thromboxane by commercially available enzyme-linked immunoassays [Caymen Chemical Co., Ann Arbor, Mich.]. Test compounds which inhibit 5-lipoxygenase in this assay inhibit the formation of $LTB_4$ and cause reduced levels of this agent in the supernatant. Test compounds which also inhibit cyclooxygenase in this assay also cause reduced levels of thromboxane in the supernatant.

The results for this assay are presented in Table 1 hereinbelow. The results of this assay are expressed in terms of activity with respect to 5-lipoxygenase inhibition as an $IC_{50}$ value (50% inhibitory concentration).

TABLE 1

| Compound Number | Example Number | Recombinant 5-Lipoxygenase Inhibition Assay $IC_{50}$ (μM) | TPA (Mouse, Ear) (50 mpk, ip + 120 minute) Edema (% Inhibition) | TPA (Mouse, Ear) (50 mpk, ip + 120 minute) MPO (% Inhibition) | Human Whole Blood Assay $LTB_4$ $IC_{50}$ (μM) | Human Whole Blood Assay Thromboxane $IC_{50}$ (μM) |
|---|---|---|---|---|---|---|
| 5 | 3 | 0.57 ± 0.07 | 42 | 24 | 13.3 | 50 |
| 8 | 6 | 4.48 + 0.36 | *— | — | — | — |
| 14 | 11 | 0.41 ± 0.02 | — | — | — | — |
| 15 | 12 | 0.49 ± 0.04 | — | — | 6.27 | 14.4 |
| 16 | 12 | 03.4 ± 0.10 | — | — | — | — |
| 18 | 13 | 0.32 ± 0.02 | — | — | — | — |
| 19 | 13 | 0.36 ± 0.07 | — | — | 6.62 | >39 |
| 21 | 14 | 0.14 ± 0.02 | — | — | 2.26 | 18.6 |
| 24 | 16 | 0.48 ± 0.09 | — | — | — | — |
| 26 | 17 | 0.93 ± 0.16 | — | — | 11.1 | 9.1 |

TABLE 1-continued

| | | Recombinant 5-Lipoxygenase | TPA (Mouse, Ear) (50 mpk, ip + 120 minute) | | Human Whole Blood Assay | |
|---|---|---|---|---|---|---|
| Compound Number | Example Number | Inhibition Assay $IC_{50}$ (μM) | Edema (% Inhibition) | MPO | $LTB_4$ $IC_{50}$ (μM) | Thromboxane $IC_{50}$ (μM) |
| 27 | 18 | 1.1 ± 0.23 | 46 | — | 7.42 | 37.3 |
| 29 | 20 | 1.8 ± 0.3 | — | — | 20.1 | 50 |

*— = not calculated

(7) EXAMPLES

The following non-limiting examples further describe and illustrate details from the preparation of the compounds of the present invention from readily available starting materials. Those skilled in the art will readily understand and appreciate that known variations of the conditions and procedures in the following preparative methods can be utilized.

In these examples, all temperatures are degrees Celsius unless otherwise noted. Melting points were determined on a Fisher-Johns melting point apparatus or by DSC and are uncorrected.

Unless indicated otherwise in a particular example or biological evaluation, all of the starting materials, and all of the equipment, employed in the examples and biological evaluations are commercially available. Sources for these materials include Sigma Chemical Co. (St. Louis, Mo.), Aldrich Chemical Co. (Milwaukee, Wis.), Lancaster Synthesis (Windham, N.H.), Bioproducts For Science, Inc. (Indianapolis, Ind.), Fisher Scientific (Pittsburgh, Pa.), Boehringer Mannheim Biochemicals (Indianapolis, Ind.), Fluka Chemical Corp. (Ronkonkoma, N.Y.), TCI, American Tokyo Kasei, Inc. (Atlanta, Ga.), Chemical Dynamics Corp. (South Plainfield, N.J.), Amano International Enzyme Company, Inc. (Troy, Va.), Nu-Chek-Prep, Inc. (Elysian, Minn.), Cayman Chemical (Ann Arbor, Mich.), Cistron (Pine Brook, N.J.), Gibco/BRL (Gaithersburg, Md.) and Invitrogen (Palo Alto, Cailf.). Most of the starting materials were obtained from Aldrich Chemical Co. (Milwaukee, Wis.). The syntheses of those starting materials which are not commercially available are described in the examples presented below.

All patents and publications referred to in the examples, and throughout the specification, are hereby incorporated herein by reference, without admission that such is prior art.

Example 1

2,6-bis(1,1-dimethylethyl)-4-[(3-hydroxypropyl)thio]phenol (2)

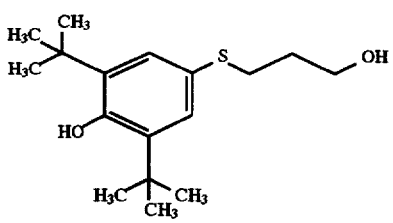

To a solution of 2,6-bis(1,1-dimethyl)-4-mercaptophenol 1 (13.6 g, 57 mmol) in DMF (150 ml), anhydrous potassium carbonate (15.76 g, 114 mmol) and 3-bromopropanol (5.3 ml) were added. After stirring at room temperature for 20 hours, the reaction mixture was filtered and the filter cake was washed with methylene chloride. The combined filtrates were concentrated and the crude orange solid (14 g) obtained was chromatographed (silica gel; hexane/ethyl acetate 7/3) to give 2 (9.93 g, 59%) as a pale orange liquid. The structural assignment was supported by the $^1$H-NMR spectrum in $CDCl_3$.

Example 2

4-[(3-brompropropyl)thio]-2,6bis(1,1-dimethylethyl)phenol (3)

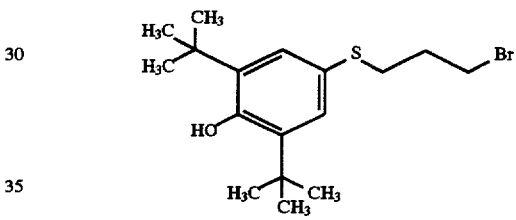

Triphenylphosphine (17.54 g, 66.89 mmol) was added to a stirred solution of 2 (9.9 g, 33.44 mmol) and carbon tetrabromide (22.18 g, 66.89 mmol) in dry ether. After stirring at room temperature for 18 hours, the reaction mixture was concentrated and the crude product was chromatographed (silica gel; hexane/ethyl acetate 98/2) to give 3 in quantitative yield. The structural assignment was supported by the $^1$H-NMR spectra in $CDCl_3$.

Example 3

2,6-bis(1,1-dimethylethyl)-4-[[3-(5H-imidazo-[4,5-c]pyridin-5-yl)propyl]thio]phenol (5)

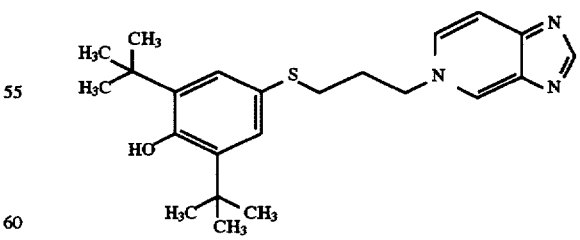

A solution of 3 (1.08 g, 3.0 mmol) and imidazo[4,5-c]pyridine 4 (538 mg, 4.5 mmol) in dimethylformamide (30 ml) was heated at 70° C. After 20 hours, the solvent was removed and the crude residue (1.54 g) was chromatographed (silica gel; methylene chloride/methanol/ ammonium hydroxide 90/10/1) to give 5 (745 mg, 62%) as a crystalline solid. mp (DSC) 181° C. The structural assignment was supported by the ¹H-NMR spectrum. Analysis calculated for $C_{29}H_{31}N_3OS \cdot 0.75\ H_2O$: C, 67.20; H, 7.97; N, 10.22; S, 7.80. Found: C, 66.85; H, 7.67; N, 10.08; S, 7.44.

Example 4

2,6-bis(1,1-dimethylethyl)-4-[(2-hydroxyethyl)thio] phenol (6)

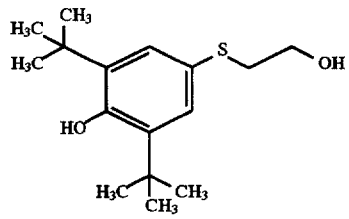

To a stirred mixture of $K_2CO_3$ (52.2 g, 0.378 mol) in a solution of 1 (100.0 g, 0.373 mol) in DMF (900 ml) at room temperature was added bromoethanol (28.2 ml, 0.378 mol). After 6 hours, the reaction was recharged with an additional 6 ml of bromoethanol and stirred for one additional hour. The reaction was concentrated in vacuo, poured onto water, and extracted several times with ethyl acetate. The combined ethyl acetate layers were dried ($Na_2SO_4$), filtered and evaporated to yield a brown oil. The crude product was chromatographed on silica gel using mixtures of ethyl acetate and hexane as eluents. The oil thus obtained was crystallized under hexane to give 83.93 g (78.7%) of crystalline product in two crops, mp 62.6°–65°. An analytical sample was obtained by recrystallization from hexane. The structural assignment was supported by the ¹H NMR spectrum. Analysis calculated for $C_{16}H_{26}O_2S$: C, 68.04; H, 9.28; S, 11.35. Found: C, 68.06; H, 9.46; S, 11.44.

Example 5

4-[(2-bromoethyl)thio]-2,6-bis(1,1-dimethylethyl) phenol (7)

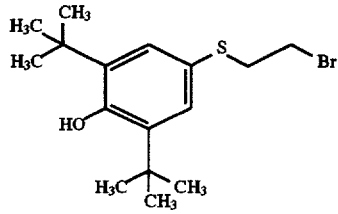

Triphenylphosphine (3.72 g, 14.2 mmol) was added to a stirred solution of 6 (2.0 g, 7.1 mmol) and carbon tetrabromide (4.7 g, 14.2 mmol) in dry ether (80 ml). After stirring at room temperature for 16 hours, the reaction mixture was concentrated and the crude product was chromatographed (silica gel; hexane/ethyl acetate 95/5) to give 7 (2.1 g, 82%) as a crystalline solid. mp (DSC) 112° C. Analysis calculated for $C_{16}H_{25}BrOS$: C, 55.65; H, 7.30; Br, 23.14; S, 9.28. Found C, 55.49; H, 7.27; Br, 22.10; S, 9.36.

Example 6

2,6-bis(1,1-dimethylethyl)-4-[[2-(5H-imidazo-[4,5-c]pyridin-5-yl)ethyl]thio]-phenol hydrate (8)

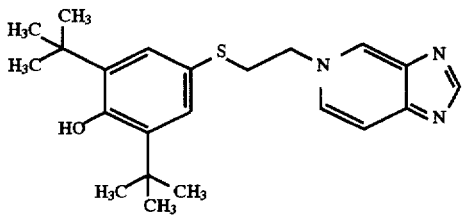

A solution of 7 (1.1 g, 3.9 mol) and imidazo[4,5-c]pyridine 4 (464 mg, 3.9 mmol) in dimethylacetamide (40 ml) was heated at 70° C. After 48 hours, the solvent was removed and the crude residue (1.2 g) was chromatographed (silica gel; methylene chloride/methanol/ammonium hydroxide 90/10/1) to give 8 (252 mg, 17%) as a crystalline solid. mp (DSC) 196° C.

Analysis calculated for $C_{22}H_{29}N_3OS \cdot 0.25\ H_2O$: C, 68.09; H, 7.66; N, 10.86; S, 8.26. Found: C, 68.17; H, 7.93; N, 10.66; S, 8.23.

Example 7

2,6-bis(1,1-dimethylethyl)-4-[[3-(1,3-dioxolan-2-yl)propyl)]thio]phenol (10)

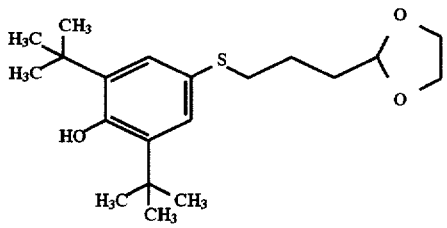

To a solution of 1 (15 g, 63 mmol) in acetone (300 ml), anhydrous potassium carbonate (17.4 g, 126 mmol) and 2-(3-chloropropyl)-1,3-dioxalane 9 (9.9 ml) were added. After stirring at room temperature for 48 hours, the reaction mixture was filtered and the filter cake was washed with more acetone. The combined filtrates were concentrated and the crude black liquid (25.7 g) was chromatographed (silica gel; hexane/ethyl acetate 9/1) to give 13.8 g of a mixture of product 10 and starting material 9 (7:3). This mixture was used in the next example without further purification.

Example 8

4-[[3,5-bis(1,1-dimethylethyl)-4-hydroxyphenyl]thio]butanal (11)

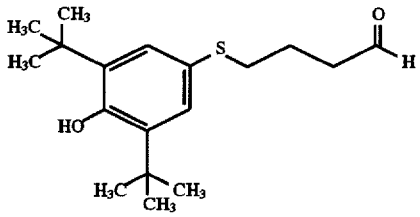

A mixture of crude 10 (13.1 g) as obtained in Example 7 was heated in acetic acid (180 ml) and water (120 ml) at 70°–75° C. After 4 hours, the reaction mixture was cooled to room temperature and then poured onto ether. The ethereal layer was separated and washed with water, an aqueous sodium bicarbonate solution and brine. After drying over MgSO$_4$, the ethereal fractions were filtered and concentrated. The crude residue (11.8 g) was chromatographed (silica gel: hexane/ethyl acetate 9/1) to give 11 (6.1 g) as a colorless liquid. Analysis calculated for C$_{18}$H$_{28}$O$_2$S·0.4. H$_2$O: C, 68.42; H, 9.20; S, 10.16. Found: C, 68.42; H, 8.76; S, 10.65.

Example 9

2,6-bis(1,1-dimethylethyl)-4-[(4-hydroxybutyl)thio]phenol(12)

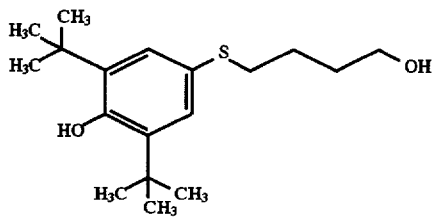

To a solution of 11 (5.72 g, 18.57 mmol) in ethanol (20 ml), sodium borohydride (2.1 g, 55.7 mmol) was added and the mixture was refluxed for 5 hours. The reaction mixture was cooled to room temperature and then quenched by adding an excess of water. After extraction in methylene chloride (2×500), the organic layer was washed (with brine), dried (over MgSO$_4$) and filtered. The solvent was removed from the organic fractions and the crude residue (6.2 g) was chromatographed (silica gel; hexane/ethyl acetate 75/25) to give 12 (4.52 g, 78%) as a colorless liquid. The structural assignment was supported by the $^1$H-NMR spectrum. Analysis calculated for C$_{18}$H$_{30}$O$_2$S·0.25H$_2$O: C, 68.63; H, 9.76; S, 10.18. Found: C, 68.50; H, 9.48; S, 10.28.

Example 10

4-[(4-bromobutyl)thio]-2,6-bis(1,1-dimethylethyl)phenol (13)

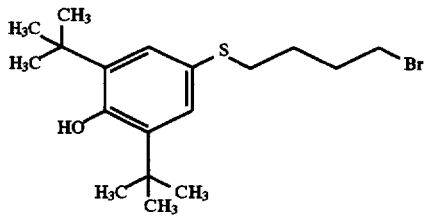

Triphenylphosphine (1.69 g, 6.45 mmol) was added to a stirred solution of 12 (1.0 g, 3.22 mmol) and carbon tetrabromide (2.14 g, 6.45 mmol) in dry ether (50 ml). After stirring at room temperature for 18 hours, the reaction mixture was concentrated and the crude product chromatographed (silica gel; hexane/ethyl acetate 90/10) to give 13. The structural assignment was supported by the $^1$H-NMR spectrum.

Example 11

2,6-bis(1,1-dimethylethyl)-4-[[4-(5H-imidazo-[4,5-c]pyridin-5-yl)butyl]thiophenol hydrate (14)

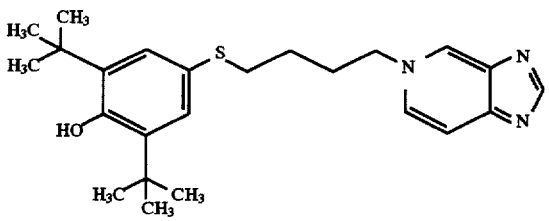

A solution of 13 (2.0 g, 5.36 mmol) and imidazo[4,5-c]pyridine 4 (640 mg, 5.36 mmol) in dimethylacetamide (40 ml) was heated at 70° C. After 48 hours, the solvent was removed. The crude residue was redissolved in methylene chloride and washed with aqueous potassium carbonate and brine. The organic fractions were dried over MgSO$_4$, filtered and concentrated. The residue obtained (2.9 g) was chromatographed (silica gel; methylene chloride/methanol/ammonium hydroxide 90/10/1) to give 14 (510 mg, 23%). Analysis calculated for C$_{24}$H$_{33}$N$_3$OS·0.25H$_2$O: C, 69.28; H, 8.11; N, 10.10; S, 7.71. Found: C, 69.05; H, 8.22; N, 9.84; S, 7.80.

Example 12

2,6-bis(1,1-dimethylethyl)-4-[[3-(1H-imidazo[5,4-c]pyridin-1-yl)propyl]-thio]phenol (15)

2,6-bis(1,1-dimethylethyl)-4-[[3-(1H-imidazo[4,5-c]pyridin-1-yl)propyl]-thio]phenol (16)

2,6-bis(1,1-dimethylethyl)-4-[[3-(5H-imidazo-[4,5-c]pyridin-5-yl)propyl]thio]phenol (5)

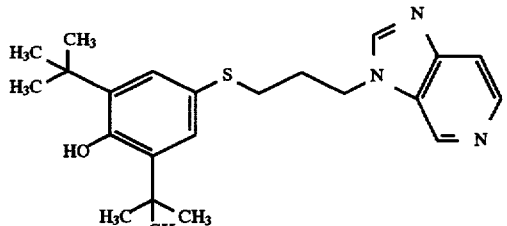

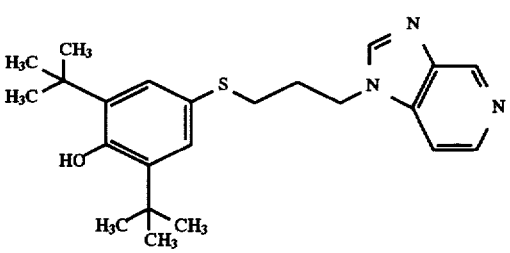

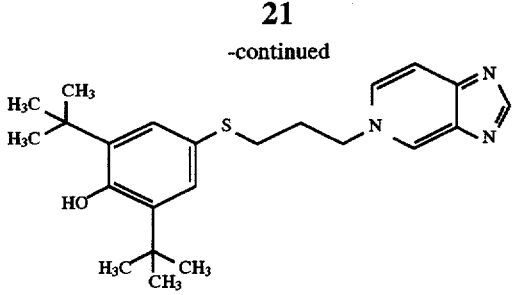

To a solution of imidazopyridine 4 (5 g, 42 mmol) in dimethylformamide (250 ml), sodium hydride (2.01 g, 60% dispersion in mineral oil, 50.4 mmol) was added. After stirring for 1 hour at 20° C., 1-chloro-3-iodopropane (5.42 ml, 50.4 mmol) was added over 10 minutes. The reaction mixture was stirred for 24 hours and then the phenol 1 (14 g, 58 mmol) was added over 5 minutes. After stirring for an additional 48 hours, the reaction mixture was poured over ice and extracted with methylene chloride. The organic layer was separated, washed (brine), dried ($MgSO_4$), filtered and concentrated. The crude product was chromatographed (silica gel; methylene chloride/methanol/ammonium hydroxide 95/5/0.5) to give 15, 16 and 5, respectively. The structural assignments were supported by the $^1$H-NMR spectrum.

15: mp (DSC) 132° C.; Analysis calculated for $C_{23}H_{31}N_3OS$: C, 69.48; H, 7.86; N, 10.57; S, 8.06. Found C, 69.16; H, 7.72; N, 10.31; S, 8.03.

16: mp (DSC) 131° C; Analysis calculated for $C_{23}H_{31}N_3OS$: C, 69.48; H, 7.86; N, 10.57; S, 8.06. Found C, 69.17; H, 7.91; N, 10.53; S, 7.96.

Example 13

(2,6-bis(1,1-dimethylethyl)-4-[[3-(1H-imidazo[5,4-b]pyridin-1-yl)propyl]thio]-phenol hydrate (18)

2,6-bis(1,1-dimethylethyl)-4-[[3-(1H-imidazo[4,5-b]pyridin-1-yl)propyl]thio]-phenol hydrate (19)

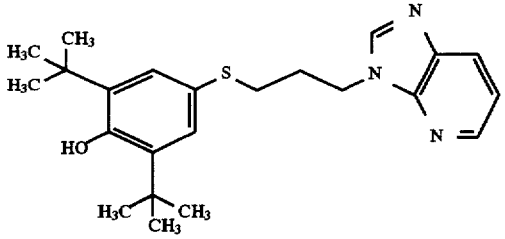

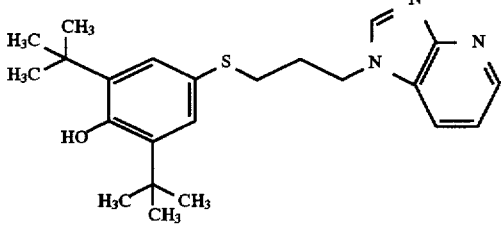

To a solution of imidazopyridine 17 (5 g, 42 mmol) in dimethylformamide (250 ml) was added sodium hydride (2.01 g, 60% dispersion in mineral oil, 50.4 mmol). After stirring for 1 hour at 20° C., 1-chloro-3-iodopropane (5.42 ml, 50.4 mmol) was added over 10 minutes. The reaction mixture was stirred for 24 hours and then the phenol 1 (12.8 g, 54 mmol) was added over minutes. After stirring for an additional 48 hours, the reaction mixture was poured over ice and extracted with methylene chloride. The organic layer was separated, washed (brine), dried ($MgSO_4$), filtered and concentrated. The crude product (24.8 g) was chromatographed (silica gel; methylene chloride/methanol/ammonium hydroxide 95/5/0.5) to give 18 & 19 respectively. The structural assignments were supported by the $^1$H-NMR spectrum.

18: mp (DSC) 97° C.; Analysis calculated for $C_{29}H_{31}N_3OS \cdot 0.25H_2O$: C, 68.70; H, 7.90; N, 10.45; S, 7.97. Found: C, 68.58; H, 7.70; N, 10.28; S, 7.95.

19: mp (DSC) 113° C.; Analysis calculated for $C_{23}H_{31}N_3OS \cdot 0.75H_2O$: C, 67.20; H, 7.97; N, 10.22; S, 7.80. Found: C, 67.53; H, 7.72; N, 9.95; S, 7.68.

Example 14

2,6-bis(1,1-dimethylethyl)-4-[[3-(1H-benzimidazol-1-yl)propyl]thio]phenol (21)

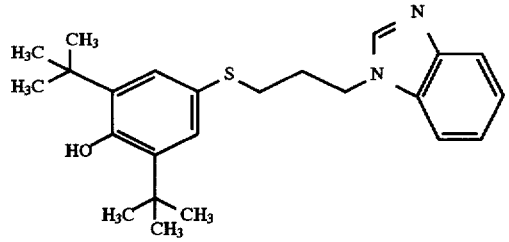

To a solution of benzimidazole 20 (5 g, 42 mmol) in dimethylformamide (200 ml) was added sodium hydride (2.01 g, 60% dispersion in mineral oil, 50.4 mmol). After stirring for 1 hour at 20° C., 1-chloro-3-iodopropane (5.42 ml, 50.4 mmol) was added over 10 minutes. The reaction mixture was stirred for 24 hours and then the phenol 1 (14 g, 58 mmol) and triethylamine (7 ml) were added over 5 minutes. After stirring for an additional 48 hours, the reaction mixture was poured over ice and extracted with methylene chloride. The organic layer was separated, washed (brine), dried ($MgSO_4$), filtered and concentrated. The crude product (31 g) was chromatographed (silica gel; methylene chloride/methanol/ammonium hydroxide 95/5/0.5) to give 21 (7.43 g, 45%). mp (DSC) 96° C. Analysis calculated for $C_{24}H_{23}N_2OS$: C, 72.68; H, 8.13; N, 7.06; S, 8.08. Found: C, 72.51; H, 8.18; N, 7.02; S, 8.06.

Example 15

1-(3-chloropropyl)-1H-indole (23)

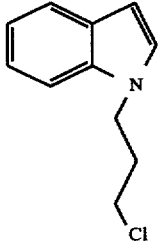

To a solution of indole 22 (5 g, 42 mmol) in dimethylformamide (200 ml) was added sodium hydride (2.01 g, 60% dispersion in mineral oil, 50.4 mmol). After stirring for 1 hour at 20° C., 1-chloro-3-iodopropane (5.42 ml, 50.4 mmol) was added over 10 minutes. The reaction mixture was stirred for 24 hours and then poured over ice and extracted with methylene chloride. The organic layer was separated, washed (brine), dried (MgSO₄), filtered and concentrated. The crude product (25.3 g) was chromatographed (silica gel; hexane/ethyl acetate 95/5) to give 23 (4.02 g, 49%). The structural assignment was supported by the ¹H-NMR spectra in CDCl₃.

Example 16

2,6-bis(1,1-dimethylethyl)-4-[[3-(1H-indol-1-yl) propyl]thio]phenol hydrate (24)

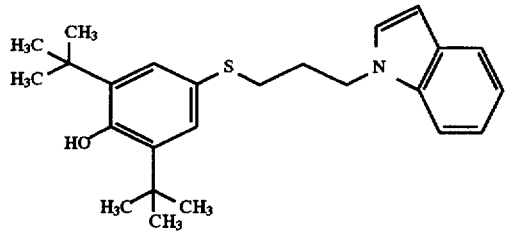

To a solution of 23 (4.02 g, 20.7 mmol) and 1 (4.92 g, 20.7 mmol) in dimethylformamide (100 ml), triethylamine (5.76 ml, 41.36 mol) was added. After stirring for 72 hours, the reaction mixture was poured over ice and extracted with methylene chloride. The organic layer was separated, washed (brine), dried (MgSO₄), filtered and concentrated. The crude product (8.44 g) was chromatographed (silica gel; hexane/ethyl acetate 95/5) to give 24 (2.86 g, 34%) as a colorless liquid. The structural assignment was supported by the ¹H-NMR spectrum. Analysis calculated for C₂₅H₃₃NOS·0.25H₂O: C, 75.05; H, 8.44; N, 3.50; S, 8.01. Found: C, 74.88; H, 8.32; N, 3.47; S, 7.69.

Example 17

2,6-bis(1,1-dimethylethyl)-4-[[2-[(1,3-benzoxazol-2-yl)thio]ethyl]thio]phenol hydrate (26)

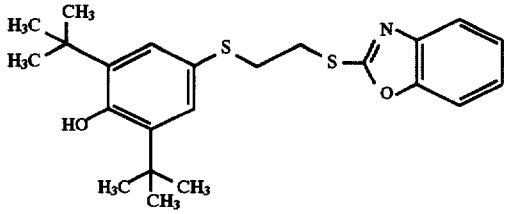

To a solution of 2-mercaptobenzoxazole 25 (460 mg, 3 mmol) in dimethylformamide (30 ml), silver tetrafluoroborate (584 mg, 3 mmol) was added. After 5 minutes, 7 (1.04 g, 3 mmol) was added and the mixture continued to stir under argon at room temperature. After 18 hours, the reaction mixture was filtered and the residue was washed with methylene chloride. The combined filtrates were concentrated and the crude yellowish liquid (4 g) obtained was chromatographed (silica gel; hexane/ethyl acetate 95/5) to give 26 (210 mg, 17%) as a crystalline solid. mp (DSC) 118° C.

Analysis calculated for C₂₃H₂₉NO₂S₂·0.4H₂O: C, 65.34; H, 7.10; N, 3.31; S, 15.17. Found: C, 65.38; H, 6.70; N, 3.22; S, 14.98.

Example 18

(±) 2,6-bis(1,1-dimethylethyl)-4-[[2-hydroxy-3-(5H-imidazo[4,5-c]pyridin-5-yl)propyl-thio]phenol hydrate (27)

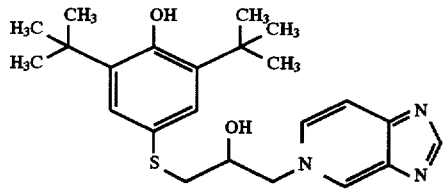

A solution of 2,6-di-t-butyl-4-(2'-hydroxy-3'-chloropropyl)thiophenol (3 g, 9 mmol) and 1(H)-imidazo(4,5c)pyridine (2.1 g, 18 mmol) in DMA (30 mls) was heated to 70° C. for 14 hours under N₂. The solvent was removed via high vacuum and the residue was treated with CH₂Cl₂ and H₂O. The organic layer was dried (Na₂SO₄) and solvent removed. The residue was chromatographed with 15 MeOH/ 85 CH₂Cl₂/0.5 NH₄OH. The product 27 (1.6 g, 43%) had a melting point of 185°–187° C. An analytical sample was obtained by recrystallization from MeOH/H₂O. C₂₃H₃₁N₃O₂S·1/2 H₂O M.W.=422.59. Analysis Calculated for C₂₃H₃₁N₃O₂S·1/2 H₂O: C, 65.37; H, 7.63; N, 9.94; S, 7.59. Found: C, 64.94; H, 8.05; N, 9.61; S, 7.59.

Example 19

6-[[1,3-bis(dimethylethyl)-4-hydroxy phenyl]-thiomethyl]-1-methyl-1H-quinolin-2-one (28)

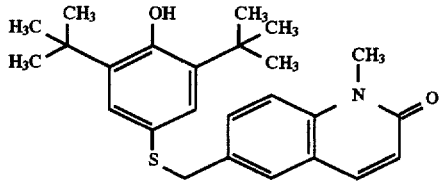

(a) 1,6-Dimethylquinoline methylsulfate (28a):

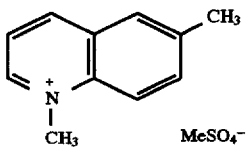

A solution of 6-methylquinoline (39 g, 0.272 mol) and dimethyl sulfate (30 mls, 0.29 mol) in toluene (400 ml) was stirred rapidly using mechanical stirring at 60° C. The resulting thick paste was diluted with more toluene, cooled to 25° C. and filtered. The product (60 g, 82%) was dried in a vacuum oven at 40° C. overnight. As this material was very hydroscopic, it was stored in a dessicator over P₂O₅.

(b) 1,6-Dimethyl-guinolin-2-one (28b)

A solution of the salt 28a (60 g, 0.22 moles) and potassium ferricyanide (147 g, 0.45 mol) in water (300 ml) was stirred rapidly as a solution of NaOH (27 g, 0.68 mol) in water (100 mls) was added slowly over 45 minutes, maintaining a reaction temperature of 50° C. After cooling, the mixture was extracted with CH₂Cl₂, dried (MgSO₄) and evaporated. The resulting crude solid was recrystallized from benzene to give pure title compound 28b (23.7 g, 62%). The structural assignment was supported by the ¹H-NMR spectrum.

Analysis Calculated for $C_{11}H_{11}NO$: C, 76.28; H, 6.40; N, 8.09. Found: C, 76.31; H, 6.45; N, 7.99.

(c) 6-Bromomethyl-1-methylquinoline-2-one (28c)

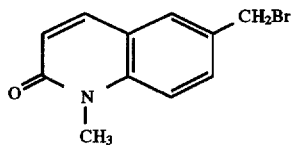

A stirred solution of 28b (22 g, 0.127 mol) and N-bromosuccinimide (23 g, 0.13 mol) in CCl₄ (400 mls) was irradiated for 2.5 hours with a 275 watt heat lamp after an addition of AIBN (50 mg) to initiate the free radical reaction. During this time, the reaction achieved reflux. After cooling, the mixture was concentrated to a small volume and ethyl acetate (400 mls) and water (150 mls) were added and the layers separated. The organic phase was dried (MgSO₄) and evaporated. The crude material was purified by chromatography on silica gel using 35% ethyl acetate/toluene to give the product 28c (10.4 g, 33%) as a solid, mp 99°–100° C. The structural assignment was supported by the ¹H-NMR spectrum. Analysis calculated for $C_{11}H_{10}NOBr$: C, 52.41; H, 4.00; N, 5.56; Br, 31.69. Found: C, 52.11; H, 3.91; N, 5.40; Br, 31.40.

(d) 6-[[1,3-bis(dimethylethyl)-4-hydroxy phenyl]-thiomethyl]-1-methyl-1H-quinolin-2-one (28)

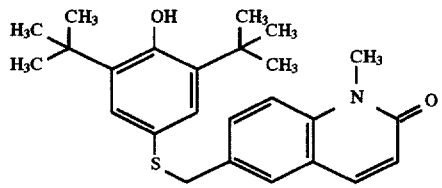

A mixture of K₂CO₃ (850 mg, 6.2 mmol) in a solution of 28c (750 mg, 0.3 mmol) and 2,6-di-t-butyl-4-mercaptophenol (1 g, 3 mmol) in DMF (25 ml) was stirred for 4 hours at 25° C. The mixture was filtered and the filtrate was evaporated in vacuo using an oil pump. The residue was dissolved in ethyl acetate, washed with water and the organic layer was dried (Na₂SO₄). After evaporation, the residue was chromatographed on silica gel with 40% ethyl acetate/hexane to give pure product (950 mg, 77%) as a solid, mp 135°–136° C. The structural assignment was supported by the 1H-NMR spectrum.

Analysis calculated for $C_{25}H_{31}NO_2S$: C, 73.31; H, 7.63; N, 3.42; S, 7.83. Found: C, 73.28; H, 7.52; N, 3.36; S, 7.57.

Example 20

2,6-bis(1,1-dimethylethyl)-4-[[(3H-imidazo-[4,5-b]pyridin-2-yl)methyl]thio]phenol (29)

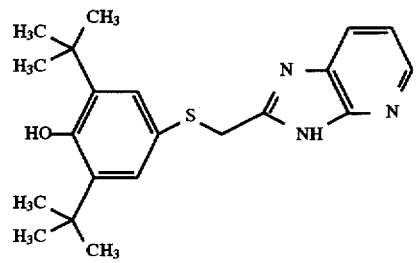

(a) 2-Chloromethyl-1(H)-imidazo[4,5-b]pyridine (29a)

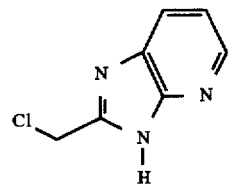

To a slurry of 2-hydroxymethyl-1(H)-imidazo[4,5-b]pyridine (2 g, 13 mmol) in EtOH (5 mls) was added a solution of HCl in dioxane (4M in HCl, 10 ml, 40 mmol). This was stirred for 10 minutes, and the crude hydrochloride salt was filtered. This salt was slurried in CHCl₃ (15 ml), thionyl chloride (5 ml) was added and the mixture was refluxed for 48 hours. The reaction mixture was filtered hot and evaporated. The crude product was used without further purification.

(b) 2,6-bis(1,1-dimethylethyl)-4-[[(3H-imidazo-[4,5-b]pyridin-2-yl)methyl]thio]phenol (29)

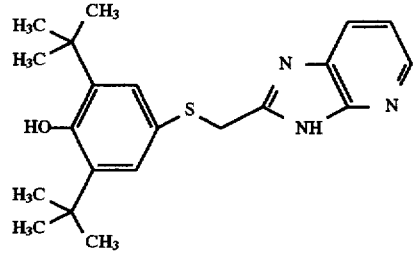

A mixture of K₂CO₃ (10 g), crude 29a (2.6 g, 12 mmol) and 2,6-di-t-butyl-4-mercaptophenol (5 g, 21 mmol) in DMF (50 mls) was stirred for 16 hours at 25° C. The reaction was filtered and the filtrate was concentrated in vacuo using an oil pump. The residue was chromatographed on silica gel using MeOH:CH₂Cl₂:NH₂OH (5:94:1) as the eluent to give the purified product 29 (3 g, 80%) as a crystalline solid, mp 241°–242° C. The structural assignment was supported by the ¹H-NMR spectrum. Analysis calculated for $C_{21}H_{27}N_3OS$: C, 68.26; H, 7.36; N, 11.37; S, 8.68. Found: C, 67.91; H, 7.44; N, 10.97; S, 8.69.

| Compound No. | Compound Structure |
|---|---|
| 1 | 2,6-di-tert-butyl-4-mercaptophenol |
| 2 | 4-[(3-hydroxypropyl)thio]-2,6-di-tert-butylphenol |
| 3 | 4-[(3-bromopropyl)thio]-2,6-di-tert-butylphenol |
| 4 | 1H-imidazo[4,5-c]pyridine |
| 5 | 4-[[3-(imidazo[4,5-c]pyridin-5-yl)propyl]thio]-2,6-di-tert-butylphenol |
| 6 | 4-[(2-hydroxyethyl)thio]-2,6-di-tert-butylphenol |
| 7 | 4-[(2-bromoethyl)thio]-2,6-di-tert-butylphenol |

| Compound No. | Compound Structure |
|---|---|
| 8 | 2,6-di-tert-butyl-4-[(2-(imidazo[4,5-c]pyridin-5-yl)ethyl)thio]phenol |
| 9 | 2-(3-chloropropyl)-1,3-dioxolane (chloro-alkyl dioxolane) |
| 10 | 2,6-di-tert-butyl-4-[[3-(1,3-dioxolan-2-yl)propyl]thio]phenol |
| 11 | 4-[(3,5-di-tert-butyl-4-hydroxyphenyl)thio]butanal |
| 12 | 4-[(3,5-di-tert-butyl-4-hydroxyphenyl)thio]butan-1-ol |
| 13 | 2,6-di-tert-butyl-4-[(4-bromobutyl)thio]phenol |
| 14 | 2,6-di-tert-butyl-4-[[4-(imidazo[4,5-c]pyridin-5-yl)butyl]thio]phenol |

-continued

| Compound No. | Compound Structure |
| --- | --- |
| 15 | 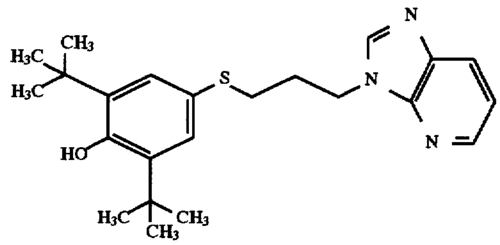 |
| 16 | 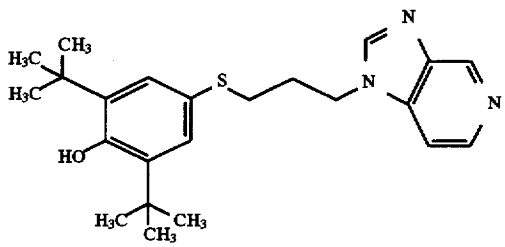 |
| 17 | 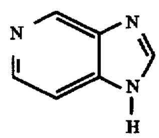 |
| 18 | 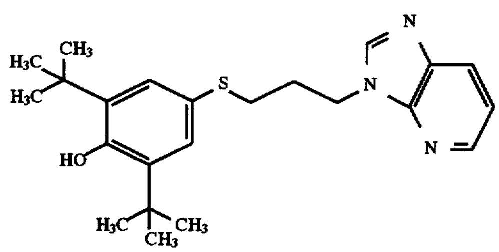 |
| 19 | 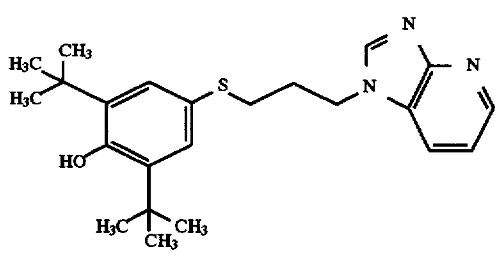 |
| 20 | 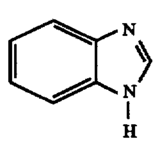 |
| 21 | 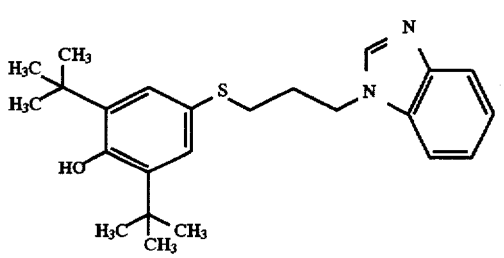 |

-continued

| Compound No. | Compound Structure |
|---|---|
| 22 | benzimidazole (1H-benzimidazole) |
| 23 | 1-(3-chloropropyl)indole |
| 24 | 3,5-di-tert-butyl-4-hydroxyphenyl-S-(CH$_2$)$_3$-N-indole |
| 25 | 2-mercaptobenzoxazole (HS-benzoxazole) |
| 26 | 3,5-di-tert-butyl-4-hydroxyphenyl-S-CH$_2$CH$_2$-S-benzoxazol-2-yl |
| 27 | 3,5-di-tert-butyl-4-hydroxyphenyl-S-CH$_2$-CH(OH)-CH$_2$-N(imidazo[4,5-c]pyridine) |
| 28 | 3,5-di-tert-butyl-4-hydroxyphenyl-S-CH$_2$-(1-methyl-2-oxo-1,2-dihydroquinolin-6-yl) |
| 28a | 1,6-dimethylquinolinium MeSO$_4^-$ |

-continued

| Compound No. | Compound Structure |
|---|---|
| 28b | 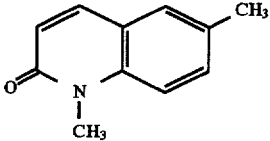 |
| 28c | 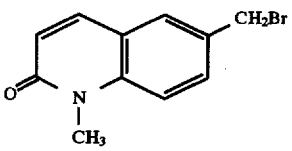 |
| 29 | 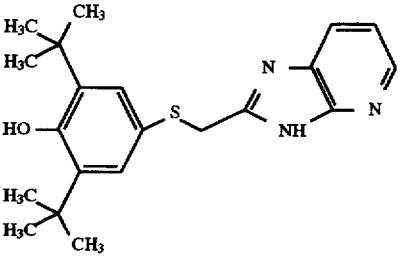 |
| 29a | 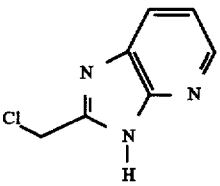 |

The foregoing examples are provided to enable one of ordinary skill in the art to practice the present invention. These examples are merely illustrative, however, and should not be read as limiting the scope of the invention as it is claimed in the appended claims.

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. For example, effective dosages other than the preferred ranges set forth hereinabove may be applicable as a consequence of variations in the responsiveness of the animal being treated, dosage-related adverse effects, if any, and analogous considerations. Likewise, the specific pharmacological responses observed may vary according to, and depending upon, the particular active compound selected, or whether there are present certain pharmaceutical carriers, as well as the type of formulation and mode of administration employed. Such expected variations and/or differences in the results are contemplated in accordance with the objects and practices of the present invention. It is intended therefore that all of these modifications and variations be within the scope of the present invention as described and claimed herein, and that the invention be limited only by the scope of the claims which follow, and that such claims be interpreted as broadly as is reasonable.

What is claimed is:

1. A compound of the formula:

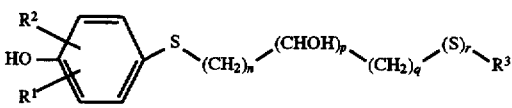

or a pharmaceutically acceptable salt thereof, wherein:
$R^1$ and $R^2$ are each alkyl;
n is an integer of from 1 to 5;
p is an integer of from 0 to 1;
q is an integer of from 0 to 3;
r is an integer of from 0 to 1; and
$R^3$ is

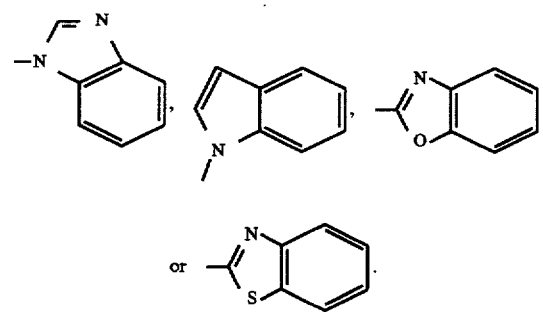

2. A compound of claim 1 wherein $R^1$ and $R^2$ are tert-butyl.

3. A compound of claim 2 where p is 0.

4. A compound of claim 3 wherein q and r are each 0.

5. A compound of claim 1 having the structure:

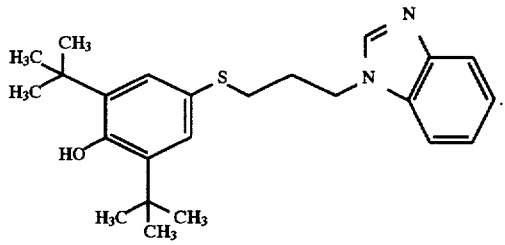

6. A compound of claim 1 having the structure:

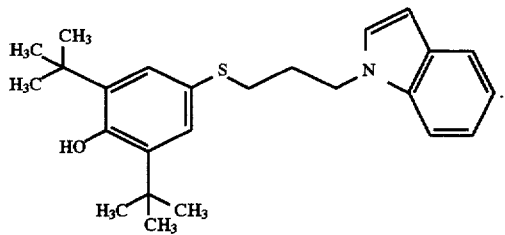

7. A compound of claim 1 having the structure:

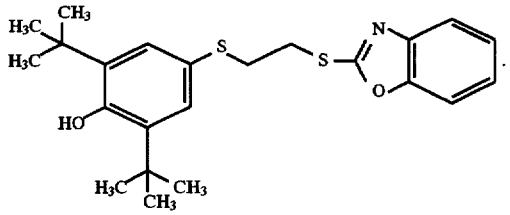

8. A pharmaceutical composition comprising a pharmaceutically-acceptable carrier and a pharmaceutically-effective amount of a compound of the formula:

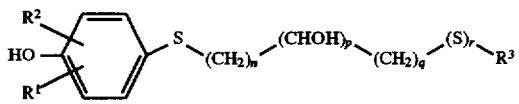

or a pharmaceutically acceptable salt thereof, wherein $R^1$ and $R^2$ are each alkyl;

n is an integer of from 1 to 5;

p is an integer of from 0 to 1;

q is an integer of from 0 to 1; and $R^3$ is

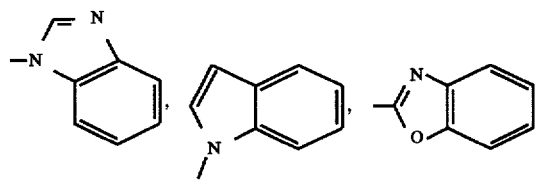

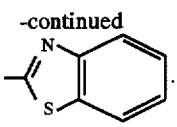

9. The pharmaceutical composition of claim 8 wherein the compound is chosen from the group consisting of:

2,6-bis(1,1-dimethylethyl)-4-[[3-(1H-benzimidazol-1-yl)propyl]thio]phenol (21);

2,6-bis(1,1-dimethylethyl)-4-[[3-(1H-indol-1-yl)propyl]thio]phenol hydrate (24); and 2,6-bis(1,1-dimethylethyl)-4-[[2-[(1,3-benzoxazol-2-yl)thio]ethyl]thio]phenol hydrate (26).

10. A method for treating 5-lipoxygenase mediated conditions in an animal in need of such treatment comprising administering to the animal a therapeutically-effective amount of a compound of the formula:

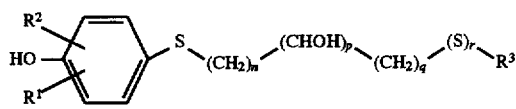

or a pharmaceutically acceptable salt thereof, wherein:

$R^1$ and $R^2$ are each alkyl;

n is an integer of from 1 to 5;

p is an integer of from 0 to 1;

q is an integer of from 0 to 3;

r is an integer of from 0 to 1; and $R^3$ is

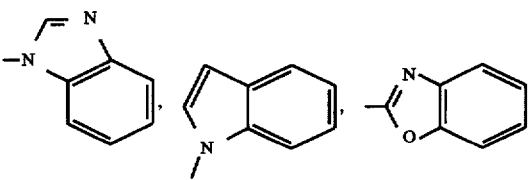

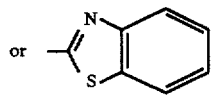

11. The method of claim 10 wherein the compound is chosen from the group consisting of:

2,6-bis(1,1-dimethylethyl)-4-[[3-(1H-benzimidazol-1-yl)propyl]thio]phenol (21);

2,6-bis(1,1-dimethylethyl)-4-[[3-(1H-indol-1-yl)propyl]thio]phenol hydrate (24); and 2,6-bis(1,1-dimethylethyl)-4-[[2-[(1,3-benzoxazol-2-yl)thio]ethyl]thio]phenol hydrate (26).

12. A method for treating a 5-lipoxygenase mediated inflammation-associated disorder or an allergy in an animal in need of such treatment comprising administering to the animal a therapeutically-effective amount of a compound of the formula:

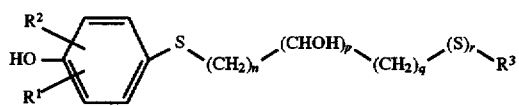

or a pharmaceutically acceptable salt thereof, wherein:

$R^1$ and $R^2$ are each alkyl;

n is an integer of from 1 to 5;

p is an integer of from 0 to 1;

q is an integer of from 0 to 3;

r is an integer of from 0 to 1; and $R^3$ is

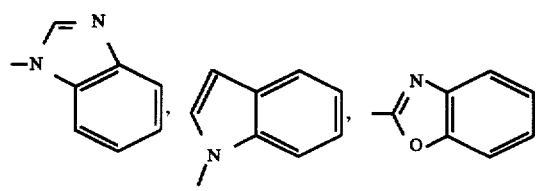

or 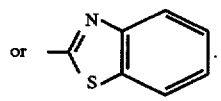

13. The method of claim 12 wherein the compound is chosen from the group consisting of:

2,6-bis(1,1-dimethylethyl)-4-[[3-(1H-benzimidazol-1-yl)propyl]thio]phenol (21);

2,6-bis(1,1-dimethylethyl)-4-[[3-(1H-indol-1-yl)propyl]thio]phenol hydrate (24); and 2,6-bis(1,1-dimethylethyl)-4-[[2-[1,3-benzoxazol-2-yl)thio]ethyl]thio]phenol hydrate (26).

* * * * *